(12) United States Patent
Schieferstein et al.

(10) Patent No.: US 7,318,929 B2
(45) Date of Patent: Jan. 15, 2008

(54) COSMETIC PREPARATIONS

(75) Inventors: Ludwig Schieferstein, Ratingen (DE); Werner Seipel, Hilden (DE); Joachim Conradi, Duesseldorf (DE); Dagmar Goebels, Voerde (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 737 days.

(21) Appl. No.: 10/474,572

(22) PCT Filed: Apr. 3, 2002

(86) PCT No.: PCT/EP02/03703

§ 371 (c)(1),
(2), (4) Date: Oct. 10, 2003

(87) PCT Pub. No.: WO02/088212

PCT Pub. Date: Nov. 7, 2002

(65) Prior Publication Data
US 2004/0115158 A1 Jun. 17, 2004

(30) Foreign Application Priority Data
Apr. 12, 2001 (DE) ................. 101 18 269

(51) Int. Cl.
A61Q 19/10 (2006.01)
A61Q 5/02 (2006.01)
A61Q 5/12 (2006.01)

(52) U.S. Cl. .................. 424/401; 424/70.11

(58) Field of Classification Search ............ None
See application file for complete search history.

(56) References Cited

U.S. PATENT DOCUMENTS

| | | | |
|---|---|---|---|
| 4,155,892 A | 5/1979 | Emmons et al. | |
| 4,172,887 A | 10/1979 | Vanlerberghe et al. | |
| 5,252,696 A | 10/1993 | Laas et al. | |
| 5,705,169 A | 1/1998 | Stein et al. | |
| 5,730,960 A | 3/1998 | Stein et al. | |
| 5,945,091 A | 8/1999 | Habeck et al. | |
| 6,090,876 A | 7/2000 | Edelmann et al. | |
| 6,162,774 A * | 12/2000 | Charlton et al. | 510/130 |
| 6,193,960 B1 | 2/2001 | Metzger et al. | |

FOREIGN PATENT DOCUMENTS

| | | |
|---|---|---|
| CA | 13 41 003 | 9/1987 |
| DE | 1 081 225 | 5/1960 |
| DE | 1165574 | 8/1960 |
| DE | 20 24 051 | 12/1971 |
| DE | 2 054 885 | 5/1972 |
| DE | 36 30 319 | 3/1988 |
| DE | 197 12 033 A1 | 9/1998 |
| DE | 197 56 377 A1 | 6/1999 |
| EP | 0 693 471 B1 | 1/1996 |
| EP | 0 694 521 B1 | 1/1998 |
| EP | 0 818 450 A1 | 1/1998 |
| EP | 0 922 447 | 6/1999 |
| FR | 2 252 840 A | 6/1975 |
| GB | 962 919 | 7/1964 |
| GB | 1 333 475 | 10/1973 |
| GB | 1 358 430 | 7/1974 |

OTHER PUBLICATIONS

B. Salka, "Alkyl Polyglycosides", Cosmetics & Toiletries, vol. 108, Mar. 1993, pp. 89-94.
Lochhead et al., "Encyclopedia of Polymers and Thickeners", Cosmetics & Toiletries, vol. 108,(1993), pp. 95-135.
Todd et al., "Volatile silicone fluids for cosmetic formulations", Cosmetics & Toiletries, vol. 91,(1976), pp. 29-32.

* cited by examiner

Primary Examiner—Jyothsna Venkat
(74) Attorney, Agent, or Firm—John F. Daniels; Daniel S. Ortiz

(57) ABSTRACT

A cosmetic composition containing a polyether urethane thickener corresponding to formula I:

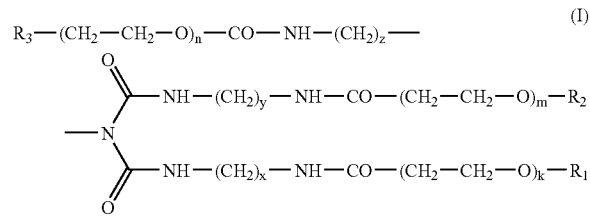

wherein $R^1$, $R^2$ and $R^3$ independently of one another, represent linear or branched alkyl and/or alkenyl groups containing from about 6 to 22 carbon atoms, x, y and z, independently of one another, represent a number from 1 to 10 and k, m and n, independently of one another, represent a number from about 10 to 200.

18 Claims, No Drawings

COSMETIC PREPARATIONS

BACKGROUND OF THE INVENTION

This application is a 371 of PCT/EP02/03703 filed Apr. 3, 2002.

This invention relates generally to cosmetic products and, more particularly, to preparations containing polyether urethanes as viscosity- and consistency-increasing factors.

Polyether urethanes are polymers which are obtained by reaction of alcohol ethoxylates with isocyanates or polyisocyanates.

These compounds have been used for decades in the printing industry. Polyether urethanes differ very considerably in their physico-chemical properties according to the starting materials used and the stoichiometric ratio between them. In printing pastes for pigment printing, they improve the lubricity of the emulsions used (DE-AS 1 081 225). In printing pastes, diisocyanates reacted with ethoxylated aliphatic alcohols having an ethylene oxide degree of 60 to 400 produce a viscosity which enables the quantity of organic solvent used to be reduced (DE-OS 2 054 885) and which leads to brilliant prints. If thickeners containing aromatic diisocyanates are used in these printing pastes, the advantageous properties of the printing pastes can be further improved.

The use of these thickeners in aqueous systems is described in DE 36 30 319 A1. However, in order to obtain readily processable, low-viscosity and shear-resistant substances instead of the above-mentioned thickeners, which represent paste-form, firm products, the polyether urethanes used were prepared from a mixture of ethylene oxide and propylene oxide and aliphatic alcohols with diisocyanates in a fixed molar ratio.

The thickeners used in cosmetic and body care preparations have to meet stringent requirements. First and foremost, they have to show high compatibility and also—if possible—biodegradability so that many substances have to be ruled out from the outset for use in cosmetics. In addition, they should be universally useable in aqueous, emulsoidal, alcoholic and oil-containing bases, readily processable and lead to a rheology which enables the product to be easily applied so that the preparations can be removed and distributed under clean and simple conditions. They are expected to be compatible with many other auxiliaries, more particularly with salts and surfactants. The thickener itself and the other auxiliaries should also lend themselves to incorporation. The thickened preparations are also expected to show stable rheology and an unchanging physical and chemical quality even in the event of long-term storage and changes in pH and temperature. Finally, the thickeners should be inexpensive to produce without causing significant environmental pollution.

In view of this complex requirement profile, it is clear why, even today, there is still a demand for new thickeners in the cosmetics field.

Accordingly, the problem addressed by the present invention was to provide cosmetic formulations which, after addition of only small quantities of a thickener, would be easy to apply and would leave the skin with a pleasant feeling. The formulations would be easy to distribute on the skin and in the hair without leaving a feeling of stickiness behind. They would have improved physical and chemical stability and would be highly compatible with the skin and scalp. In addition, the viscosity and consistency factors would be unaffected by additions of ions and other auxiliaries or by changes in pH and temperature.

DESCRIPTION OF THE INVENTION

The present invention relates to cosmetic preparations containing polyether urethane thickeners corresponding to formula (I):

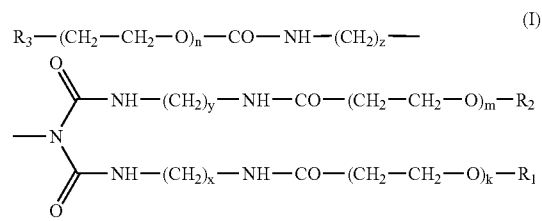

in which $R^1$, $R^2$ and $R^3$ independently of one another represent linear or branched alkyl and/or alkenyl groups containing 6 to 22 carbon atoms, x, y and z independently of one another stand for numbers of 1 to 10 and k, m and n independently of one another stand for numbers of 10 to 200, and to their use in the care and cleaning of the skin and hair.

It has surprisingly been found that cosmetic preparations in which polyether urethanes are used as viscosity- and consistency-increasing factors show advantageous rheological behavior. Even in small quantities, the polyether urethanes used have an excellent thickening effect. Even systems with low surfactant contents can be thickened. The rheology of the formulations remains unchanged even after prolonged storage and despite changes in temperature. The formulations are highly compatible with the skin and scalp. The small quantities of polymers lead to a pleasant, non-sticky feeling on the skin so that hair fibers are also prevented from sticking together. The preparations show high physical and chemical stability, even with high salt concentrations.

Polyether Urethanes

Polyether urethanes are polymers which are obtained by reaction of alcohol ethoxylates with isocyanates or polyisocyanates.

Alcohol ethoxylates are known from their production as fatty alcohol or oxoalcohol ethoxylates and preferably correspond to formula (II):

in which $R^1$ is a linear or branched alkyl and/or alkenyl group containing 6 to 22 carbon atoms and n is a number of 1 to 200. Typical examples of the alcohol ethoxylates used in the polyether urethanes according to the invention are the adducts of, on average, 10 to 200, preferably 30 to 150 and more particularly 80 to 120 mol ethylene oxide with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Adducts of 40 to 60 mol ethylene oxide with technical $C_{12-18}$ fatty alcohols such as, for example, coconut oil, palm oil, palm kernel oil or tallow fatty alcohol, more especially $C_{16-18}$ fatty alcohols, are preferred.

The isocyanates used may be aliphatic polyisocyanates, preferably diisocyanates containing 1 to 10 methylene groups and preferably 4 to 8 methylene groups. A particularly preferred diisocyanate is hexamethylene diisocyanate which may also be linked to cyclic multiples of hexamethylene diisocyanate, such as the commercially available Isocyanurat T 1890® of Degussa and more especially the trifunctional aliphatic hexamethylene diisocyanate obtainable under the name of Desmodur RF® from Bayer. Where cyclic polyisocyanates are used, polyurethanes corresponding to formula (VI) are formed.

Another particularly preferred isocyanate is the reaction product of a hexamethylene diisocyanate half-hydrolyzed to the monoamine with one isocyanate group of each of another two hexamethylene diisocyanates to (III):

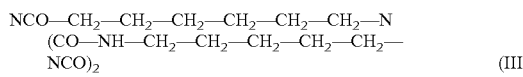

$\text{NCO—CH}_2\text{—CH}_2\text{—CH}_2\text{—CH}_2\text{—CH}_2\text{—CH}_2\text{—N}$
$(\text{CO—NH—CH}_2\text{—CH}_2\text{—CH}_2\text{—CH}_2\text{—CH}_2\text{—}$
$\text{NCO})_2$ (III)

The polyether urethanes may be produced by the methods described in DE 36 30 319 A1. Another process which is particularly important for the thickeners of the preparations according to the invention in that it allows simple, inexpensive and rapid production is described in the Examples of the present specification. It is a process in which ethoxylated fatty alcohols are predried, a cyclized diisocyanate is then added to them under nitrogen in a reflux apparatus at 90 to 100° C. and preferably at 95 to 105° C. and a reaction time of up to 3 hours, preferably 2 hours and more particularly only one hour is needed to reach an NCO value below 0.1% by weight and preferably below 0.05% by weight. It is particularly advantageous that the reaction does not require a catalyst and that the reaction time is very short.

The average molecular weight of the polyether urethanes used for the purposes of the invention is in the range from 4,000 to 30,000, preferably in the range from 8,000 to 20,000 and more particularly in the range from 10,000 to 15,000.

The preparations according to the invention may contain the polyether urethanes in quantities of 0.01 to 5% by weight, preferably in quantities of 0.05 to 3% by weight and more particularly in quantities of 0.1 to 1% by weight, based on the formulation as a whole.

Depending on the composition and the nature of the cosmetic preparation, the viscosity of the formulation can be adjusted to an exact value through the choice of the polyether urethanes of corresponding molecular weight via the ethylene oxide units. Depending on the thickened formulation, viscosities in the range from 100 to 1,000,000 mpa·s, preferably in the range from 1,000 to 50,000 mPa·s and more particularly in the range from 4,000 to 35,000 mPa·s (Brookfield RVT viscosimeter, 10 r.p.m., spindle 4, room temperature) can be adjusted.

Surfactant solutions in particular can be effectively thickened with the selected polyether urethanes, a combination with alk(en)yl oligoglycosides and/or alk(en)yl sulfates having proved to be particularly effective in terms of the stability and compatibility of the formulations.

Alkyl and/or Alkenyl Oligoglycosides

Alkyl and/or alkenyl oligoglycosides are known nonionic surfactants which correspond to formula (IV):

$R^1O\text{—}[G]_p$ (IV)

where $R^1$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The overviews presented by Bierman et al. in Starch/Stärke 45, 281 (1993), by B. Salka in Cosm. Toil. 108, 89 (1993) and by J. Kahre et al. in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (IV) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

The preparations according to the invention may contain alkyl and/or alkenyl oligoglycosides in quantities of 0.1 to 30, preferably 1 to 20 and more particularly 5 to 10% by weight, based on the formulation as a whole.

Alkyl and/or Alkenyl Sulfates

Alkyl and/or alkenyl sulfates, which are also often referred to as fatty alcohol sulfates, are the sulfation products of primary alcohols which correspond to formula (V):

$R^1O\text{—}SO_3X$ (V)

in which $R^1$ is a linear or branched, aliphatic alkyl and/or alkenyl group containing 6 to 22 and preferably 12 to 18 carbon atoms and X is an alkali metal and/or alkaline earth metal, ammonium, alkylammonium, alkanolammonium or glucammonium. Typical examples of alkyl sulfates which may be used for the purposes of the invention are the sulfation products of caproic alcohol, caprylic alcohol, capric alcohol, 2-ethylhexyl alcohol, lauryl alcohol, myristyl alcohol, cetyl alcohol, palmitoleyl alcohol, stearyl alcohol,

isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained by high-pressure hydrogenation of technical methylester fractions or aldehydes from Roelen's oxo-synthesis. The sulfation products may advantageously be used in the form of their alkali metal salts, more particularly their sodium salts. Alkyl sulfates based on $C_{16/18}$ tallow fatty alcohols or vegetable fatty alcohols of comparable C-chain distribution in the form of their sodium salts are particularly preferred.

The preparations according to the invention may contain alkyl and/or alkenyl sulfates in quantities of 0.1 to 20% by weight and preferably in quantities of 1 to 15% by weight, based on the formulation as a whole.

Commercial Applications

The cosmetic preparations thickened using the polyether urethanes in accordance with the invention are used for the care, protection and cleaning of the skin and hair and, accordingly, represent cosmetic and/or pharmaceutical preparations such as, for example, hair shampoos, hair lotions, foam baths, shower baths, creams, gels, lotions, alcoholic and aqueous/alcoholic solutions, emulsions, wax/fat compounds, stick preparations, powders or ointments. These preparations may also contain mild surfactants, oil components, emulsifiers, pearlizing waxes, consistency factors, thickeners, superfatting agents, stabilizers, polymers, silicone compounds, fats, waxes, lecithins, phospholipids, biogenic agents, UV protection factors, antioxidants, deodorizers, antiperspirants, antidandruff agents, film formers, swelling agents, insect repellents, self-tanning agents, tyrosine inhibitors (depigmenting agents), hydrotropes, solubilizers, preservatives, perfume oils, dyes and the like as further auxiliaries and additives.

Other Surfactants

Suitable surfactants are anionic, nonionic, cationic and/or amphoteric or zwitterionic surfactants which are normally present in the preparations in quantities of about 1 to 70, preferably 5 to 50 and more particularly 10 to 30% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethion-ates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, fatty acid glucamides, alkylamidobetaines, amphoacetals and/or protein fatty acid condensates, preferably based on wheat proteins.

Oil Components

Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol, esters of $C_{18-38}$ alkylhydroxycarboxylic acids with linear or branched $C_{6-22}$ fatty alcohols (cf. DE 197 56 377 A1), more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv®

TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols, silicone oils (cyclomethicone, silicon methicone types, etc.) and/or aliphatic or naphthenic hydrocarbons, for example squalane, squalene or dialkyl cyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide ontolinear $C_{8-22}$ fatty alcohols, $C_{12-22}$ fatty acids and alkyl phenols containing 8 to 15 carbon atoms in the alkyl group and alkylamines containing 8 to 22 carbon atoms in the alkyl group (independently of the compounds reacted beforehand with isocyanates to form thickeners);

adducts of 1 to 15 mol ethylene oxide with castor oil and/or hydrogenated castor oil;

adducts of 15 to 60 mol ethylene oxide with castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and adducts thereof with 1 to 30 mol ethylene oxide;

partial esters of polyglycerol (average degree of self-condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and adducts thereof with 1 to 30 mol ethylene oxide;

mixed esters of pentaerythritol, fatty acids, citric acid and fatty alcohol according to DE 1165574 PS and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethylene glycol-30 Dipolyhydroxystearate;

polymer emulsifiers, for example Pemulen types (TR-1, TR-2) of Goodrich;

polyalkylene glycols and glycerol carbonate.

Ethylene Oxide Addition Products

Other addition products of ethylene oxide and/or propylene oxide with fatty alcohols, fatty acids, alkylphenols or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as lipid layer enhancers for cosmetic formulations from DE 20 24 051 PS. These ethylene oxide addition products may be present in the formulation alongside the molecules reacted with isocyanates to form thickeners.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric and Cationic Emulsifiers

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{,12/18}$ acyl sarcosine. Finally, other suitable emulsifiers are cationic surfactants, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Thickeners

Besides the polyether urethanes according to the invention, other consistency factors and thickeners may be used. The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Stabilizers Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR 2252840 A and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacryl-amide/methyl methacrylate/tert.-butylaminoethyl methacrylate/2-hydroxy-propyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones. Other suitable polymers and thickeners can be found in Cosm. Toil., 108, 95 (1993).

Silicone Compounds

Suitable silicone compounds are, for example, dimethyl polysilox-anes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives as described in EP 0694521 B1.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione and the enamine compounds described in DE 19712033 A1 (BASF). The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments are preferably used in sun protection products. Micronized zinc oxide is preferably used. Other suitable UV filters can be found in P. Finkel's review in SÖFW-Journal 122, 543 (1996) and in Parf. Kosm. 3, 11 (1999).

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prune extract, bambara nut extract, and vitamin complexes.

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'-trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, lemon balm oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants

Antiperspirants reduce perspiration and thus counteract underarm wetness and body odor by influencing the activity of the eccrine sweat glands. Aqueous or water-free antiperspirant formulations typically contain the following ingredients:
astringent active principles,
oil components,
nonionic emulsifiers,
co-emulsifiers,
consistency factors,
auxiliaries in the form of, for example, thickeners or complexing agents and/or
non-aqueous solvents such as, for example, ethanol, propylene glycol and/or glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine. Oil-soluble and water-soluble auxiliaries typically encountered in antiperspirants may also be present in relatively small amounts. Oil-soluble auxiliaries such as these include, for example,
inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH adjusters, for example buffer mixtures, water-soluble thickeners, for example water-soluble natural or synthetic polymers such as, for example, xanthan gum, hydroxyethyl cellulose, polyvinyl pyrrolidone or high molecular weight polyethylene oxides.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1 H-imidazol-1-ylmethyl)-1,3-dioxylan-c-4-yl-methoxy-phenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Insect Repellents Suitable insect repellents are N,N-diethyl-m-toluamide, pentane-1,2-diol or Ethyl Butylacetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, kojic acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are
glycerol;
alkylene glycols such as, for example, ethylene glycol, diethylene glycol, propylene glycol, butylene glycol, hexylene glycol and polyethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipenta-erythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formal-dehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, lso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, eucalyptus oil, fennel oil, citrus oil, wintergreen oil, clove oil, menthol and the like.

Dyes

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. Examples include cochineal red A (C.l. 16255), patent blue V (C.l. 42051), indigotin (C.l. 73015), chlorophyllin (C.l. 75810), quinoline yellow (C.l. 47005), titanium dioxide (C.l. 77891), indanthrene blue RS (C.l. 69800) and madder lake (C.l. 58000). Luminol may also be present as a luminescent dye. These dyes are normally used in concentrations of 0.001 to 0.1% by weight, based on the mixture as a whole.

The total percentage content of auxiliaries and additives may be from 1 to 99% by weight and is preferably from 5 to 40% by weight, based on the particular preparations. The preparations may be produced by standard hot or cold processes and are preferably produced by the phase inversion temperature method.

EXAMPLES

The following Examples are intended to illustrate the invention without limiting it in any way. The polyether urethane described under the heading "production" was used in the Examples of Tables 1, 2 and 3.

Production of a Polyether Urethane of Formula (I) According to the Invention

This polyether urethane is a polyurethane of stearyl alcohol·100 EO (Brij 700 P, Unichema) and trimerized hexamethylene diisocyanate (Desmodur N 3300 K, BAYER, Leverkusen; one each of the two NCO groups of three hexamethylene diisocyanate molecules are joined together by a (—CO—NR—)$_3$ six-membered ring) in a molar ratio of 3.15:1.

1. Predrying

Apparatus:

Vacuum distillation: 4-necked round-bottomed flask, stirrer, heat source (oil bath), contact thermometer, oil pump, cold trap Procedure:

The stearyl alcohol·100 EO (Brij 700 P, Unichema) is heated with stirring under nitrogen to 120° C. and then freed from water for 2 h by oil pump. After purging with nitrogen, the reaction mixture is cooled to 80° C. and transferred to the reflux apparatus.

2. Reaction

Apparatus:

Reflux apparatus: 4-necked round-bottomed flask, stirrer, heat source (oil bath), contact thermometer, intensive cooler, thermometer Reaction Components:

7.8 g Desmodur N3300 K (0.0177 mol) added to 195.6 g Brij 700 P NO-AOX-NENA (0.0558 mol)

Procedure:

A gentle stream of nitrogen is passed over during the reaction phase. After heating to 100° C., the triisocyanate is added. The end point of the reaction is determined by NCO titration. An NCO value below the detection limit is reached after a reaction time of 1 hour. The reaction mixture is cooled to room temperature and placed in a container.

3. Specification

Riser Melting Point [DGF Einheitsmethode C-IV 3a (52)]: 49° C.

The following preparations were produced by mixing and homogenizing the starting materials at room temperature. The polyether urethane thickener was incorporated in the particular surfactant (Plantacare 2000 UP or Texapon ASV 50) at 40 to 50° C. The viscosity of the cleaning solutions was measured 24 hours after their preparation using a Brookfield RVT viscosimeter (10 r.p.m., spindle 4; for Example 5, spindle 5). Storage stability was subjectively evaluated after storage for 4 weeks at 20, 30 and 40° C., the parameters flow behavior and appearance being evaluated. The compositions and results are set out in Table 1. Examples 1 to 5 correspond to the invention, Examples C1 to C4 are intended for comparison.

TABLE 1

Quantities in % by weight

| | C1 | C2 | C3 | C4 | 1 | 2 | 3 | 4 | 5 |
|---|---|---|---|---|---|---|---|---|---|
| Plantacare 2000 UP | 16 | — | 16 | — | — | 16 | — | 16 | — |
| Texapon NSO | 13 | — | 13 | — | — | 13 | — | 13 | — |
| Lamepon S | 9 | — | 9 | — | — | 9 | — | 9 | — |
| Texapon ASV 50 | — | 14 | — | 14 | 14 | — | 14 | — | 14 |
| Dehyton DC | — | 9 | — | 9 | 9 | — | 9 | — | 9 |
| Arlypon F | 3 | 2 | — | — | — | — | — | — | — |
| Antil 120 | — | — | 3 | 2 | — | — | — | — | — |
| Polyether urethane* | — | — | — | — | 1 | 1 | 0.5 | 1 | 1 |
| NaCl | 1 | 1 | 1 | 1 | 1 | 1 | 1 | 2 | 1.5 |
| Water | to 100 | to 100 | to 100 | to 100 | to 100 | to 100 | to 100 | to 100 | to 100 |
| pH value | 5.5 | 5.5 | 5.5 | 5.5 | 5.5 | 5.5 | 5.5 | 5.5 | 5.5 |
| Viscosity at RT [mPa · s] | 1000 | 3300 | 3500 | 200 | 24000 | 6100 | 9300 | 7100 | 34400 |
| Appearance at RT | Clear | Clear | Clear | Clear | Clear | Clear | Clear | Clear | Clear |
| Storage stability | ++ | ++ | − | − | ++ | ++ | ++ | ++ | ++ |

INCI Name

Plantacare 2000UP:
Decyl Glucoside (Cognis GmbH, Düsseldorf)

Texapon NSO:
Sodium Laureth Sulfate (Cognis GmbH, Düsseldorf)

Lamepon S:
Potassium Cocoyl Hydrolyzed Collagen (Cognis GmbH, Düsseldorf)

TexaponASV 50:
Sodium Laureth Sulfate and Sodium Laureth 8-Sulfate and Magnesium Laureth Sulfate and Magnesium Laureth 8-Sulfate and Sodium Oleth Sulfate and Magnesium Oleth Sulfate (Cognis GmbH, Düsseldorf)

Dehyton DC:
Disodium Cocoamphodiacetate (Cognis GmbH, Düsseldorf)

Arlypon F:
Laureth-2 (Cognis GmbH, Düsseldorf)

Antil 120:
Polyethylenglycol 120 Methyl Glucose Dioleate (Goldschmidt, Essen)

Polyether Urethane*:
Polyether urethane of formulal (I), in which $R^1$ and $R^2$ =C16; x=3; m and n=100

Storage Stability
−: poor viscosity stability between 20 and 40° C.
+: slight viscosity stability between 20 and 40° C.
++: good viscosity stability between 20 and 40° C.
+++: excellent viscosity stability between 20 and 40° C.

TABLE 2

Cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Polyether urethane of formula (I) Polyether urethane | 0.8 | 0.7 | 0.4 | 1.0 | 0.3 | 1.5 | 0.3 | 0.2 | 2.0 | 0.5 |
| Texapon ® NSO Sodium Laureth Sulfate | — | — | — | — | — | — | 38.0 | 38.0 | 25.0 | — |
| Texapon ® SB 3 Disodium Laureth Sulfosuccinate | — | — | — | — | — | — | — | — | 10.0 | — |
| Plantacare ® 818 Coco Glucosides | 2.0 | — | — | — | — | — | 7.0 | 7.0 | 6.0 | — |
| Plantacare ® PS 10 Sodium Laureth Sulfate (and) Coco Glucosides | — | — | — | — | — | — | — | — | — | 16.0 |
| Dehyton ® PK 45 Cocamidopropyl Betaine | — | — | — | — | — | — | — | — | 10.0 | — |
| Emulgade ® PL 68/50 Cetearyl Glucoside (and) Cetearyl Alcohol | 4.0 | — | — | — | — | — | — | — | — | — |
| Eumulgin ® VL 75 Lauryl Glucoside (and) Polyglyceryl-2 Polyhydroxystearate (and) Glycerin | — | — | 0.8 | — | 0.8 | — | — | — | — | — |
| Lanette ® O Cetearyl Alcohol | — | 2.5 | 2.5 | 2.5 | 3.0 | 2.5 | — | — | — | — |
| Lameform ® TGI Polyglyceryl-3 Isostearate | 1.0 | — | — | 1.0 | — | — | — | — | — | — |
| Dehymuls ® PGPH Polyglyceryl-2 Dipolyhydroxystearate | — | — | — | — | 1.0 | — | — | — | — | — |
| Cutina ® GMS Glyceryl Stearate | 0.5 | 0.5 | 0.5 | 0.5 | 0.5 | 1.0 | — | — | — | — |
| Cetiol ® HE PEG-7 Glyceryl Cocoate | — | — | — | — | — | — | — | — | 1.0 | — |
| Cetiol ® J 600 Oleyl Erucate | — | — | — | — | — | — | — | — | — | — |

TABLE 2-continued

Cosmetic preparations (water, preservative to 100% by weight)

| Composition (INCI) | 1 | 2 | 3 | 4 | 5 | 6 | 7 | 8 | 9 | 10 |
|---|---|---|---|---|---|---|---|---|---|---|
| Cetiol ® OE<br>Dicaprylyl Ether | — | 1.0 | — | — | — | — | — | — | — | — |
| Cetiol ® PGL<br>Hexyldecanol (and) Hexyldecyl Laurate | — | — | — | — | 1.0 | — | — | — | — | — |
| Cetiol ® V<br>Decyl Oleate | 1.0 | — | — | 1.0 | — | — | — | — | — | — |
| Eutanol ® G<br>Octyldodecanol | — | — | 1.0 | — | — | 1.0 | — | — | — | — |
| Nutrilan ® Keratin W<br>Hydrolyzed Keratin | 2.3 | — | — | — | — | — | — | — | — | — |
| Nutrilan ® I<br>Hydrolyzed Collagen | — | — | — | 2.0 | — | — | — | — | — | — |
| Lamesoft ® LMG<br>Glyceryl Laurate (and) Potassium Cocoyl Hydrolyzed Collagen | — | — | — | — | — | — | 3.0 | 2.0 | 4.0 | — |
| Gluadin ® WK<br>Sodium Cocoyl Hydrolyzed Wheat Protein | 1.0 | 1.0 | 1.0 | 1.0 | 1.0 | 1.5 | 0.5 | 0.5 | 0.5 | 0.5 |
| Euperlan ® PK 3000 AM<br>Glycol Distearate (and) Laureth-4 (and) Cocamidopropyl Betaine | — | — | — | — | — | — | — | 3.0 | 5.0 | 5.0 |
| Generol ® 122 N<br>Soja Sterol | — | — | — | — | 1.0 | 1.0 | — | — | — | — |
| Copherol ® 1250<br>Tocopherol Acetate | — | — | 0.1 | 0.1 | — | — | — | — | — | — |
| Arlypon ® F<br>Laureth-2 | — | — | — | — | — | — | 1.0 | — | — | — |
| Sodium Chloride | — | — | — | — | — | — | 0.5 | 1.5 | 1.0 | 1.5 |

(1-4) Hair rinse,
(5-6) Hair conditioner,
(7-8) Shower bath
(9) Shower gel,
(10) Wash lotion

TABLE 3

Cosmetic preparations (water, preservative to 100% by weight)

| Composition (INCI) | 11 | 12 | 13 | 14 | 15 | 16 | 17 | 18 |
|---|---|---|---|---|---|---|---|---|
| Polyether urethane of formula (I)<br>Polyether urethane | 0.2 | 0.1 | 0.8 | 0.4 | 0.4 | 1.0 | 0.3 | 0.3 |
| Texapon ® NSO<br>Sodium Laureth Sulfate | — | 30.0 | — | — | 25.0 | — | — | — |
| Plantacare ® 818<br>Coco Glucosides | — | 10.0 | 30.0 | — | 20.0 | — | — | — |
| Plantacare ® PS 10<br>Sodium Laureth Sulfate (and) Coco Glucosides | 22.0 | — | — | 22.0 | — | — | — | — |
| Dehyton ® PK 45<br>Cocamidopropyl Betaine | 15.0 | 10.0 | 10.0 | 15.0 | 20.0 | — | — | — |
| Emulgade ® SE<br>Glyceryl Sterate (and) Ceteareth 12/20 (and) Cetearyl Alcohol (and) Cetyl Palmitate | — | — | — | — | — | 4.0 | 4.0 | — |
| Lameform ® TGI<br>Polyglyceryl-3 Isostearate | — | — | — | — | — | — | — | 3.0 |
| Dehymuls ® PGPH<br>Polyglyceryl-2 Dipolyhydroxystearate | — | — | 3.8 | — | — | — | — | — |
| Monomuls ® 90-O 18<br>Glyceryl Oleate | — | — | — | — | — | — | — | 2.0 |
| Cetiol ® HE<br>PEG-7 Glyceryl Cocoate | 2.0 | — | — | 2.0 | 5.0 | — | — | — |
| Cetiol ® OE<br>Dicaprylyl Ether | — | — | — | — | — | — | — | 5.0 |
| Cetiol ® PGL<br>Hexyldecanol and Hexyldecyl Laurate | — | — | — | — | — | — | — | 10.0 |
| Cetiol ® SN<br>Cetearyl Isononanoate | — | — | — | — | — | 3.0 | 3.0 | — |
| Cetiol ® V<br>Decyl Oleate | — | — | — | — | — | 3.0 | 3.0 | — |
| Myritol ® 318<br>Coco Caprylate Caprate | — | — | — | — | — | — | — | 5.0 |
| Lemon balm oil | — | — | 5.0 | — | — | — | — | — |
| Bees Wax | — | — | — | — | — | — | — | 7.0 |

TABLE 3-continued

Cosmetic preparations (water, preservative to 100% by weight)

| Composition (INCI) | 11 | 12 | 13 | 14 | 15 | 16 | 17 | 18 |
|---|---|---|---|---|---|---|---|---|
| Nutrilan ® Keratin W<br>Hydrolyzed Keratin | — | — | — | — | — | 40.0 | 60.0 | — |
| Nutrilan ® I<br>Hydrolyzed Collagen | — | — | — | — | 2.0 | — | — | — |
| Lamesoft ® LMG<br>Glyceryl Laurate (and) Potassium Cocoyl Hydrolyzed Collagen | — | 4.0 | — | — | — | — | — | — |
| Gluadin ® AGP<br>Hydrolyzed Wheat Gluten | 0.5 | 0.5 | — | — | — | — | — | — |
| Gluadin ® WK<br>Sodium Cocoyl Hydrolyzed Wheat Protein | 2.0 | 2.0 | 4.0 | 2.0 | 5.0 | — | — | 5.0 |
| Euperlan ® PK 3000 AM<br>Glycol Distearate (and) Laureth-4 (and) Cocamidopropyl Betaine | 5.0 | — | — | 5.0 | — | — | — | — |
| Arlypon ® F<br>Laureth-2 | — | — | 0.5 | — | — | — | — | — |
| Magnesium Sulfate Hepta Hydrate | — | — | — | — | — | — | — | 1.0 |
| Citric Acid | — | — | — | — | 0.5 | — | — | — |
| Glycerin (86% by weight) | — | — | — | — | — | 3.0 | 3.0 | 5.0 |

(11-15) Foam bath,
(16) Soft cream,
(17) Moisturizing emulsion,
(18) Night cream

The invention claimed is:

1. A cosmetic composition comprising a polyether urethane thickener corresponding to formula I:

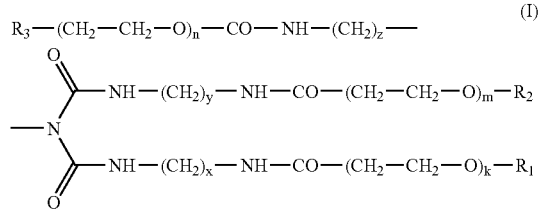

wherein $R^1$, $R^2$ and $R^3$, independently of one another, represent linear or branched alkyl and/or alkenyl groups containing from about 6 to 22 carbon atoms, x, y and z, independently of one another, represent a number from 1 to 10 and k, m and n, independently of one another, represent a number from about 10 to 200.

2. The composition of claim 1 wherein in formula I k, m and n, independently of one another, represent a number from about 80 to 120.

3. The composition of claim 1 wherein in formula I x, y and z, independently of one another, represent a number 6.

4. The composition of claim 1 wherein $R^1$, $R^2$ and $R^3$, independently of one another, represent linear or branched alkyl and/or alkenyl groups containing from about 16 to 18 carbon atoms.

5. The composition of claim 1 wherein the polyether urethane thickener is present in the composition in an amount of from about 0.01 to 5% by weight, based on the weight of the composition.

6. The composition of claim 1 wherein the polyether urethane thickener is present in the composition in an amount of from about 0.1 to 1% by weight, based on the weight of the composition.

7. The composition of claim 1 wherein the polyether urethane thickener has an average molecular weight of from about 4,000 to 30,000.

8. The composition of claim 1 wherein the composition further contains an auxiliary component selected from the group consisting of an alk(en)yl oligoglycoside, an alk(en)yl sulfate, and mixtures thereof.

9. The composition of claim 8 wherein the auxiliary is an alk(en)yl oligoglycoside present in the composition in an amount of from about 0.1 to 30% by weight, based on the weight of the composition.

10. A process for thickening a cosmetic composition used for cleaning skin and/or hair comprising adding thereto a polyether urethane thickener corresponding to formula I:

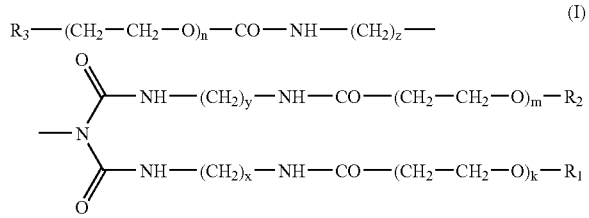

wherein $R^1$, $R^2$ and $R^3$, independently of one another, represent linear or branched alkyl and/or alkenyl groups containing from about 6 to 22 carbon atoms, x, y and z, independently of one another, represent a number from 1 to 10 and k, m and n, independently of one another, represent a number from about 10 to 200.

11. The process of claim 10 wherein in formula I k, m and n, independently of one another, represent a number from about 80 to 120.

12. The process of claim 10 wherein in formula I x, y and z, independently of one another, represent a number 6.

13. The process of claim 10 wherein $R^1$, $R^2$ and $R^3$, independently of one another, represent linear or branched alkyl and/or alkenyl groups containing from about 16 to 18 carbon atoms.

14. The process of claim 10 wherein the polyether urethane thickener is added to the composition in an amount of from about 0.01 to 5% by weight, based on the weight of the composition.

15. The process of claim 10 wherein the polyether urethane thickener is added to the composition in an amount of from about 0.1 to 1% by weight, based on the weight of the composition.

16. The process of claim 10 wherein the polyether urethane thickener has an average molecular weight of from about 4,000 to 30,000.

17. The process of claim 10 wherein the composition further contains an auxiliary component selected from the group consisting of an alk(en)yl oligoglycoside, an alk(en)yl sulfate, and mixtures thereof.

18. The process of claim 17 wherein the auxiliary is an alk(en)yl oligoglycoside present in the composition in an amount of from about 0.1 to 30% by weight, based on the weight of the composition.

* * * * *